United States Patent [19]

Souma

[11] Patent Number: 4,950,793
[45] Date of Patent: Aug. 21, 1990

[54] PROCESS FOR PREPARATION OF AROMATIC SULFONE COMPOUNDS

[75] Inventor: Yoshie Souma, Ibaraki, Japan

[73] Assignee: Agency of Industrial Science & Technology, Tokyo, Japan

[21] Appl. No.: 307,723

[22] Filed: Feb. 8, 1989

[30] Foreign Application Priority Data

Mar. 31, 1988 [JP] Japan ................................. 63-80343

[51] Int. Cl.$^5$ .......................................... C07C 147/06
[52] U.S. Cl. ...................................... 568/34; 568/28; 562/828
[58] Field of Search ..................... 568/34, 28; 562/828

[56] References Cited

U.S. PATENT DOCUMENTS 2,781,402  2/1957  Chadwick ............................. 568/34
3,579,590  5/1971  Davis .................................... 568/34

OTHER PUBLICATIONS

Graybill, Bruce M. "The Synthesis of Aryl Sulfones," *Journal of Organic Chemistry*, vol. 32, (Sep. 1967), pp. 2931–2933.

Tyobeka, Themba E., et al., "Novel Sulphonylating reagent: Sulphuric Acid–Hexafluoroacetic Anhydride," *J. C. S. Chem. Comm.*, (1980), pp. 114–115.

Sipes, Herbert J., Jr., et al., "An Improved Synthesis of Aryl Sulfones," *Synthesis*, (Mar. 1984), pp. 283–284.

Ueda, Mitsura, et al., "A New Synthesis of Diaryl Sulfones," *Synthesis*, (Apr. 1984), pp. 323–325.

Primary Examiner—Werren B. Lone
Attorney, Agent, or Firm—Armstrong, Nikaido, Marmelstein, Kubovcik & Murray

[57] ABSTRACT

An aromatic hydrocarbon represented by the following general formula [I]:

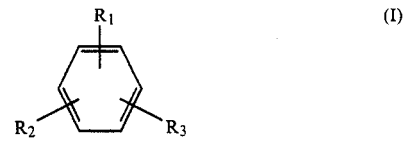

wherein $R_1$, $R_2$ and $R_3$ stand for a hydrogen atom or alkyl group, is reacted with a halogenated sulfonic acid in the presence of a Lewis acid to obtain an aromatic sulfone compound represented by the following general formula [II]:

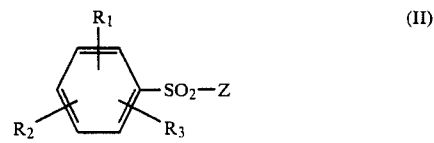

wherein $R_1$, $R_2$ and $R_3$ are as defined above and Z stands for a halogen atom or an aromatic hydrocarbon group represented by the following general formula [III]:

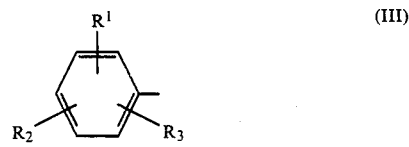

in which $R_1$, $R_2$ and $R_3$ are as defined above.

4 Claims, No Drawings

PROCESS FOR PREPARATION OF AROMATIC SULFONE COMPOUNDS

BACKGROUND OF THE INVENTION (1) Field of the Invention

The present invention relates to a process for the preparation of aromatic sulfone compounds. More particularly, the present invention relates to a process for preparing an aromatic sulfone compound, at high efficiency under mild conditions; by reacting an aromatic hydrocarbon with a halogenated sulfonic acid in the presence of a Lewis acid.

(2) Description of the Related Art

As known processes for the preparation of aromatic sulfone compounds, there can be mentioned a process in which an alkylbenzene and sulfuric acid are heated (Japanese Patent Publication No. 60-92256), a process in which an alkylbenzene-sulfonic acid and an alkylbenzene are heated in polyphosphoric acid [J. Org. Chem., 32, 2931 (1967)], and a process in which an alkylbenzenesulfonyl chloride is heated and reacted with an alkylbenzene at 140° to 220° C. in the presence of $FeCl_3$ or polyphosphoric acid (Izv. Vyssh. Ucheeb. Zaved., Khim. Khim. Tekhnol., 1969, 1588 and India J. Chem., Sect. B 1977, 1088).

However, these processes are defective in that heating is conducted for a long time, the yield is low, a large quantity of an acid solvent is used and the reaction should be carried out in multiple stages. Accordingly, these processes are not completely satisfactory as a process for preparing a sulfone compound at a low cost on an industrial scale.

Aromatic sulfone compounds or sulfonyl compounds are industrially valuable as synthetic intermediates for medicines, dyes and the like, and as starting materials for the production of polysulfone type resins. Accordingly, development of a process for preparing an aromatic sulfone compound in a shorter time and a higher yield by simpler steps with use of a smaller amount of an acid solvent is eagerly desired in the art.

SUMMARY OF THE INVENTION

It is therefore a primary object of the present invention to provide a process for the industrial preparation of an aromatic sulfone compound in which the defects of the above-mentioned known processes are eliminated.

In accordance with the present invention, this object can be attained by a process for the preparation of an aromatic sulfone compound represented by the following general formula [II]:

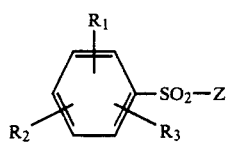

wherein $R_1$, $R_2$ and $R_3$ stand for a hydrogen atom or an alkyl group and Z stands for a halogen atom or a group represented by the following general formula (III):

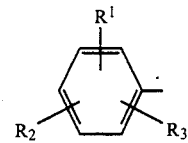

in which $R_1$, $R_2$ and $R_3$ are as defined above, which comprises reacting an aromatic hydrocarbon represented by the following formula [I]:

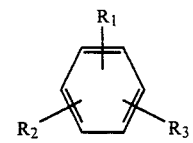

wherein $R_1$, $R_2$ and $R_3$ are as defined above, with a halogenated sulfonic acid in the presence of a Lewis acid.

DETAILED DESCRIPTION OF THE PREFERRED EMBODIMENTS

According to the present invention, an aromatic hydrocarbon is reacted with a halogenated sulfonic acid in the presence of a Lewis acid as the catalyst.

As the Lewis acid, there can be mentioned antimony halides such as antimony pentafluoride and antimony pentachloride, and tantalum pentafluoride, boron trifluoride, sulfur trioxide, arsenic pentafluoride, niobium pentafluoride, aluminum trichloride, iron trichloride and mixtures thereof. Antimony pentafluoride, antimony pentachloride and a mixture thereof are preferred.

As the halogenated sulfonic acid, there can be used halogenated fulfonic acids having a high acid strength, such as fluorosulfonic acid, chlorosulfonic acid and a mixture thereof.

According to the present invention, by the mixing of the above-mentioned Lewis acid and halogenated sulfonic acid, a super-strong acid system is formed. The acid strength of this super-strong acid is more than 100 times the acid strength of 100% sulfuric acid. Accordingly, reactions which cannot be carried out in conventional sulfuric acid or polyphosphoric acid systems become possible in case of this super-strong acid. Namely, the sulfo-cation $[SO_2F^+]$ (P) formed by the reaction (A) is present stably and makes possible an electrophilic attack on the aromatic hydrocarbon, as shown by the reaction formula (B), and therefore, the electrophilic substitution of the aromatic hydrocarbon can be easily accomplished:

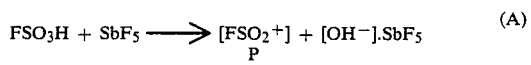

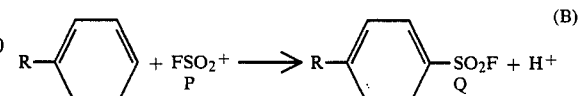

Furthermore, the Lewis acid also acts as a catalyst in the case where a sulfone compound (R) is formed from a compound (Q) (sulfornium compound), which in turn was formed by the reaction (B) or by a Friedel-Crafts reaction as shown by the following reaction (C):

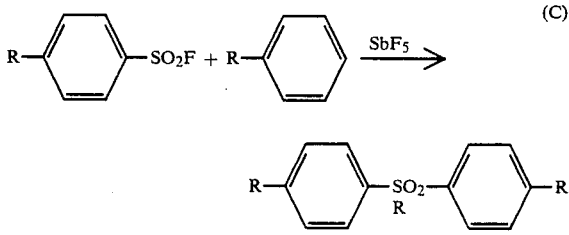

Accordingly, simply by adding an alkylbenzene to a super-strong acid, and stirring the mixture at room temperature, the sulfonation reaction is easily advanced and a sulfone compound (R) can be obtained in one stage.

The aromatic hydrocarbon used in the present invention is represented by the following general formula [I]:

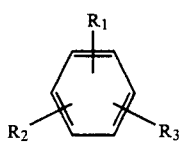

In the above-mentioned general formula [I], $R_1$, $R_2$ and $R_3$ stand for a hydrogen atom or an alkyl group, and the alkyl group has 1 to 12 carbon atoms.

As specific examples, there can be mentioned benzene, toluene, xylene, pseudocumene, mesitylene, ethylbenzene, isopropylbenzene, butylbenzene and dodecylbenzene.

As is apparent from the foregoing description, according to the present invention, only by gradually adding an aromatic hydrocarbon to a mixture of a halogenated sulfonic acid and a Lewis acid such as an antimony halide, and stirring the mixture for several hours, the sulfonation reaction is easily advanced and a sulfone compound represented by the following formula [II] is obtained:

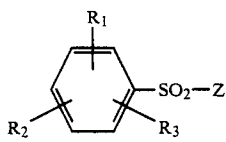

In the formula [II], $R_1$, $R_2$ and $R_3$ are as defined above with respect to the formula [I], and Z stands for a halogen atom derived from the halogenated sulfonic acid or an aromatic hydrocarbon group represented by the following general formula [III]:

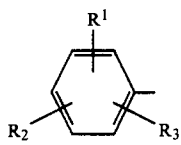

wherein $R_1$, $R_2$ and $R_3$ are as defined above with respect to the formula [I].

The reaction temperature is 20° to 80° C. and the reaction time is 2 to 24 hours. The aromatic hydrocarbon/halogenated sulfonic acid/Lewis acid molar ratio is 1/(0.2 to 5)/(0.2 to 2).

When the reaction mixture is transferred into ice water after termination of the reaction, parts of the sulfone of the formula [II] in which Z is a group of the formula [III] and the sulfonyl halide of the formula [II] in which Z is a halogen atom, are precipitated in the form of white crystals, and these precipitates are separated by filtration and washed with ethanol or ether, whereby the sulfonyl halide can be covered as white crystals. Separately, if the aqueous solution filtrate is extracted with benzene, the remaining sulfonyl chloride of the formula [II] can be recovered. The structure of the product can be confirmed by gas chromatography, NMR, IR and mass analysis.

Since solids are precipitated as the reaction proceeds, it is preferred that trifluoroacetic acid, trichloroacetic acid, dichloroacetic acid, monochloroacetic acid, acetic anhydride, sulfuric acid or the like be used as the solvent. If this solvent is used, the reaction can be advanced more easily.

As is apparent from the foregoing description, according to the present invention, since a Lewis acid is used as the catalyst and fluorosulfonic acid or chlorosulfonic acid is used as the halogenated sulfonic acid, a super-strong acid obtained by the reaction between these Lewis acid and halogenated sulfonic acid can be utilized for the sulfonation reaction.

Therefore, a desired sulfone compound can be prepared at normal temperature under atmospheric pressure very easily by one-stage reaction.

Furthermore, the process of the present invention is industrially advantageous over the conventional preparation processes in that the preparation step is simple and a high yield is attained.

The present invention will now be described in detail with reference to the following examples.

EXAMPLE 1

Into a mixture of 10 ml of fluorosulfonic acid and 6 ml of antimony pentafluoride, was dropped 8.9 ml of benzene at 25° C. over a period of 30 minutes, and the mixture was stirred for 5 hours. The reaction mixture was transferred into ice water and the precipitate was extracted with benzene to obtain 9.3 g of a yellow crude product.

From the results of the analysis of the product by gas chromatography, gas-mass spectrometry, IR and NMR, it was found that diphenylsulfone, 4-fluorodiphenylsulfone and 4,4'-difluorodiphenylsulfone were formed in yields of 60%, 25% and 5%, respectively, based on benzene.

EXAMPLE 2

Into a mixture of 10 ml of fluorosulfonic acid, 8 ml of antimony pentafluoride and 20 ml of trifluoroacetic acid, was dropped 10.5 ml of toluene at 25° C. over a period of 20 minutes. The mixture was stirred for 7 hours, and the reaction mixture was transferred into ice water. The precipitate was extracted with benzene and the extract was concentrated to obtain an oily reaction product mixture.

When the reaction product mixture was washed with methanol, 7.38 g of a white crystal (having a melting point of 148° C.) was obtained. From the results of analysis, it was confirmed that 4,4'-dimethyldiphenylsulfone and 2,2'-dimethyldiphenylsulfone were formed in yields of 50% and 10%, respectively, based on toluene.

Separately, when the methanol solution was concentrated, 5.2 g of an oily substance was obtained. From the results of analysis, it was confirmed that 4-methylphenylsulfonyl fluoride and 2-methylphenylsulfonyl fluoride were formed in yields of 18% and 12%, respectively, based on toluene.

EXAMPLE 3

Into a liquid mixture of 10 ml of fluorosulfonic acid, 8 ml of antimony pentafluoride and 20 ml of trichloroacetic acid, was gradually dropped 12 ml of xylene, and the mixture was stirred at 25° C. for 7 hours. The reaction mixture was transferred into ice water, and solids were recovered by filtration and washed with methanol to obtain 8.2 g of a white crystal having a melting point of 151° C. The yield was 60%. From the results of analysis, it was confirmed that 3,3',-4,4'-tetramethyldiphenylsulfone and its isomer were formed in yields of 50% and 10%, respectively, based on o-xylene. The remaining ice water was extracted with benzene to obtain 3,4-dimethylphenylsulfonyl fluoride and its isomer in yields of 10% and 5%, respectively, based on o-xylene.

EXAMPLE 4

Into a mixture of 10 ml of fluorosulfonic acid and 6 ml of antimonyl pentafluoride, was dropped 13.9 ml of mesitylene at 25° C., and the mixture was stirred for 5 hours. The reaction mixture was transferred into ice water and the precipitated product was extracted with benzene.

From the results of analysis, it was confirmed that 1,3,5-trimethylphenylsulfonyl fluoride and 1,1',3,3',5,5'-hexamethyldiphenylsulfone were formed in yields of 70% and 20%, respectively, based on mesitylene.

EXAMPLE 5

Into a mixture of 6.6 ml of chlorosulfonic acid, 12.6 ml of antimony pentachloride and 10 ml of dichloroacetic acid, was added 8.9 ml of benzene at 25° C., and the mixture was stirred for 5 hours. The reaction mixture was transferred into ice water and the precipitated product was extracted with benzene. From the results of analysis, it was confirmed that benzene-sulfonyl chloride and diphenylsulfone were formed in yields of 60% and 30%, respectively, based on benzene.

EXAMPLE 6

Into a mixture of 6.6 ml of chlorosulfonic acid, 6 ml of antimony pentafluoride and 10 ml of monochloroacetic acid, was added 8.9 ml of benzene at 25° C., and the mixture was stirred for 3 hours. The reaction mixture was transferred into ice water and the precipitated product was extracted with benzene. From the results of analysis, it was confirmed that benzene-sulfonyl chloride and diphenylsulfone were formed in yields of 50% and 20%, respectively, based on benzene.

EXAMPLE 7

Into a mixture of 10 ml of fluorosulfonic acid, 8 ml of antimony pentafluoride and 20 ml of trifluoroacetic acid, was dropped 12.3 g of dodecylbenzene at 25° C., and the mixture was transferred into ice water and the precipitated product was recovered by filtration to obtain a brown reaction mixture.

When this mixture was washed with methanol, 4.15 g of a yellow crystal was obtained. From the results of the analysis, it was confirmed that 4,4'-didodecyldiphenylsulfone was formed in a yield of 30% based on dodecylbenzene.

When the methanol washing solution was concentrated, 4.98 g of a brown solid was obtained. From the results of the analysis of the solid, it was confirmed that 4-dodecylphenylsulfonyl fluoride was formed in a yield of 30% based on dodecylbenzene.

What is claimed is:

1. A process for the preparation of an aromatic sulfone compound, comprising the steps of:
   (a) mixing together a Lewis acid and a halogenated sulfonic acid selected from the group consisting of chlorosulfonic acid, fluorosulfonic acid and a mixture thereof to provide a super-strong acid having the formula, $[XSO_2^+]+[OH^-] MX_n$, wherein X is a halogen atom, M is the metal atom of the Lewis acid, and n is 3 or 5;
   (b) adding an aromatic hydrocarbon having the below formula (I):

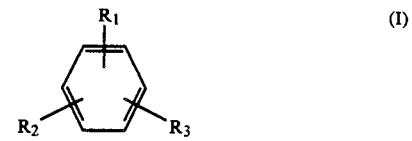

to the above provided super-strong acid;
   (c) reacting the resulting mixture at a temperature of 20° to 80° C.; and
   (d) separating an aromatic sulfone compound having the following formula (II):

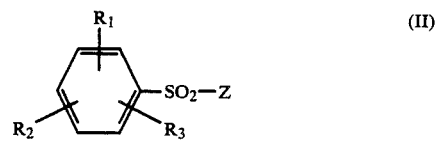

out of the resultant reaction mixture; wherein $R_1$, $R_2$ and $R_3$ are each a hydrogen atom or an alkyl group, and Z is an atom or a group selected from the group consisting of a chlorine atom, a fluorine atom and a group having the following formula (III):

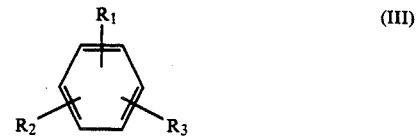

wherein $R_1$, $R_2$ and $R_3$ are as defined as above.

2. A process according to claim 1, wherein the Lewis acid is at least one compound selected from the group consisting of antimony pentafluoride, antimony pentachloride, tantalum pentafluoride, boron trifluoride, sulfur trioxide, arsenic pentafluoride, niobium pentafluoride, aluminum trichloride and iron trichloride.

3. A process according to claim 1, wherein the Lewis acid is at least one compound selected from the group consisting of antimony pentafluoride and antimony pentachloride.

4. A process according to claim 1, wherein the alkyl group has 1 to 12 carbon atoms.

* * * * *